United States Patent [19]

Garbrecht

[11] 4,356,207

[45] Oct. 26, 1982

[54] SWEETENING WITH 5-(DIHYDROXYPHENOXY) TETRAZOLES

[75] Inventor: William L. Garbrecht, Indianapolis, Ind.

[73] Assignee: Eli Lilly and Company, Indianapolis, Ind.

[21] Appl. No.: 280,661

[22] Filed: Jul. 6, 1981

Related U.S. Application Data

[62] Division of Ser. No. 123,859, Feb. 22, 1980, Pat. No. 4,309,446.

[51] Int. Cl.$^3$ ............................................. A23L 1/236
[52] U.S. Cl. ..................................... 426/548; 424/269
[58] Field of Search .......................... 426/548; 424/269

[56] References Cited

U.S. PATENT DOCUMENTS 4,309,446  1/1982  Garbrecht ...................... 426/548 X

*Primary Examiner*—Joseph M. Golian
*Attorney, Agent, or Firm*—Karen B. O'Connor; Arthur R. Whale

[57] ABSTRACT

Dihydroxyphenoxy-1H-tetrazoles and their salts are used as non-nutritive sweeteners.

15 Claims, No Drawings

SWEETENING WITH 5-(DIHYDROXYPHENOXY) TETRAZOLES

This application is a division, of application Ser. No. 123,859, filed Feb. 22, 1980 now U.S. Pat. No. 4,309,446.

BACKGROUND OF THE INVENTION

Numerous substances have been proposed and/or used as non-nutritive sweeteners; these substances do not have a caloric effect, but still impart a sweet taste. Such substances enable individuals who must limit their intake of the natural sugars to control various health conditions, including diabetes and obesity. Many of these substances or sweeteners have severe disadvantages, such as a bitter aftertaste or toxic side effects, at the same concentrations necessary to obtain the sweetening effect. Only two types of non-nutritive sweeteners are used to any extent: saccharin-type and cyclamate-type.

Other sweeteners are described in U.S. Pat. Nos. 3,087,821; 3,294,551; 3,515,727; 3,597,234; and 3,899,592. U.S. Pat. No. 3,087,821 describes the use of dihydrochalcone compounds as sweeteners. In U.S. Pat. No. 3,294,551, Herbst discloses the use of 5-carbocyclicaminotetrazole compounds and their salts as sweeteners. U.S. Pat. Nos. 3,515,727 and 3,597,234 describe monohydroxyphenoxytetrazole compounds and their salts as sweeteners. U.S. Pat. No. 3,899,592 shows that the dextro enantiomorph of certain 6-substituted tryptophane compounds can be used as sweeteners.

Since it is well known that even small changes in chemical structure will often destroy sweetening activity, the already known sweeteners do not enable one skilled in the art to predict the chemical structures of other sweeteners.

SUMMARY OF THE INVENTION

It has been discovered that 5-(dihydroxyphenoxy)-1H-tetrazole compounds of the following formula

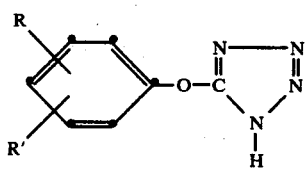

wherein R and R' are each hydroxy, and their non-toxic, physiologically-acceptable salts are useful as sweeteners or sugar substitutes. These compounds and-/or their salts can be combined with flavoring agents, medicinal substances, and other sweeteners. Also, the compounds or their salts can be administered with nutritive or non-nutritive substances, giving those substances a sweet taste.

DETAILED DESCRIPTION OF THE INVENTION

The 5-(dihydroxyphenoxy)-1H-tetrazole compounds of the formula

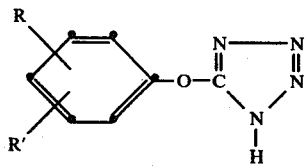

wherein R and R' are each hydroxy, are useful as sugar substitutes or sweeteners. In addition, the nontoxic, physiologically-acceptable salts of these compounds are also effective sweeteners.

The compounds of this invention are:
5-(2,3-dihydroxyphenoxy)-1H-tetrazole;
5-(2,4-dihydroxyphenoxy)-1H-tetrazole;
5-(2,5-dihydroxyphenoxy)-1H-tetrazole;
5-(2,6-dihydroxyphenoxy)-1H-tetrazole;
5-(3,4-dihydroxyphenoxy)-1H-tetrazole; and
5-(3,5-dihydroxyphenoxy)-1H-tetrazole.

The preferred compound is 5-(2,3-dihydroxyphenoxy)-1H-tetrazole.

The 5-dihydroxyphenoxy-1H-tetrazole compounds are prepared by demethylating the corresponding 5-dimethoxyphenoxy-1H-tetrazole compounds. Demethylation can be done by various means. For example, one way is to use pyridine hydrochloride neat and to heat the mixture of the 5-dimethoxyphenoxy-1H-tetrazole and pyridine hydrochloride at about 200° C. Another means of demethylation is with boron tribromide in methylene chloride. After appropriate workup, the dihydroxyphenoxy tetrazoles may be purified by crystallization from a water solution.

The preferred method of demethylation is using anhydrous aluminum chloride in a solvent such as benzene, chlorobenzene, toluene, methylene chloride, and the like. The solvent of choice is benzene. Optimal purity of the 5-dihydroxyphenoxy-1H-tetrazole compounds is obtained at a temperature of about 60° C., using three to four moles of anhydrous aluminum chloride. The reaction mixture is then hydrolyzed, preferably with a 30% solution of methanol in water. The product is extracted with a solvent such as ethyl acetate, ether, and the like and then the solvent is evaporated. The product is crystallized from water, nitroethane, or the like.

The 5-dimethoxyphenoxy-1H-tetrazole starting materials are made from the corresponding commercially available dimethoxyphenols. Triethylamine is added to the phenol and cyanogen bromide in an organic solvent, such as ether or ethyl acetate, followed by an aqueous solution of sodium azide. The aqueous phase containing the tetrazole product as a sodium salt is separated from the reaction mixture, acidified, and extracted with an appropriate solvent. After the solvent is evaporated, the product, a 5-dimethoxyphenoxy-1H-tetrazole, is crystallized.

The following examples illustrate the preparation of the dimethoxy starting materials and the claimed 5-dihydroxyphenoxy-1H-tetrazole compounds. The claimed compounds were identified by high pressure liquid chromatography. The chromatographic column (25 cm by 4 mm) was packed with silica bonded to aliphatic chains containing 18 carbons (Water's Bondapak C/18) and the compounds were detected with ultraviolet radiation at 254 nm.

EXAMPLE 1

5-(2,3-Dimethoxyphenoxy)-1H-tetrazole

To a stirred mixture of 50 g. of 2,3-dimethoxyphenol, 35 g. of cyanogen bromide and 300 ml. of ether, maintained at 10°–15° C., 47 ml. of triethylamine was added dropwise over a period of 30 minutes. A solution of 25 g. of sodium azide in 100 ml. of water was added rapidly and the mixture was heated under reflux with stirring for an hour.

The aqueous layer was separated and acidified with concentrated hydrochloric acid. A heavy oil separated out of the aqueous layer and the oil was collected by extraction with ether. The ether was evaporated and chlorobenzene was added to crystallize the product, 5-(2,3-dimethoxyphenoxy)-1H-tetrazole. The product had a melting point of about 94°–95° C., and the yield was 17.3 g. or 23%. Titration with base in 66% dimethylformamide gave the following results: $pK_a = 4.58$ and the apparent molecular weight (amw)=221 (theory 222). The following elemental analysis was obtained:

Calculated for $C_9H_{10}O_3N_4$: Theory: C, 48.65; H, 4.54; N, 25.2, Found: C, 48.63; H, 4.31; N, 25.1.

EXAMPLE 2

5-(2,6-dimethoxyphenoxy)-1H-tetrazole

Following the procedure in Example 1, 5-(2,6-dimethoxyphenoxy)-1H-tetrazole was prepared using 2,6-dimethoxyphenol as the starting material. The product obtained, 5-(2,6-dimethoxyphenoxy)-1H-tetrazole, had a melting point of about 180°–182° C., and weighed 62 g. (87% yield). The amw by titration was 226 (theory 222).

Other 5-dimethoxyphenoxy-1H-tetrazoles were prepared following the method described above, such as 5-(2,4- and 2,5-dimethoxyphenoxy)-1H-tetrazole and 5-(3,4- and 3,5-dimethoxyphenoxy)-1H-tetrazole.

Certain isomers of the 5-dihydroxyphenoxy-1H-tetrazole compounds are obtained in a mixture with other isomers. Due to the ortho hydroxy group, isomerization occurs between 5-(2,3-dihydroxyphenoxy)-1H-tetrazole and 5-(2,6-dihydroxyphenoxy)-1H-tetrazole and between 5-(2,4-dihydroxyphenoxy)-1H-tetrazole and 5-(2,5-dihydroxyphenoxy)-1H-tetrazole.

The mixture of the 2,3- and 2,6-isomers can be prepared by the method shown in Example 3. The mixture of the 2,3- and 2,6-isomers is obtained whether 5-(2,3-dimethoxyphenoxy)-1H-tetrazole or 5-(2,6-dimethoxyphenoxy)-1H-tetrazole is used as the starting material. The isomers are interconverted in a protic solvent, such a solvent is needed to break up the aluminum chloride complex and isolate the product. Preferred protic solvents are water and lower alcohols. The ratio of 2,3- to 2,6-isomer is from about 40 to 60 to about 60 to 40 in the solution. If the isomers are crystallized from a water solution, then the ratio of 2,3- to 2,6-isomer is about 75 to 25, because the 2,3-isomer is less soluble than the 2,6-isomer and crystallizes first.

A dry equilibrium mixture of the two isomers can also be made by spray-drying or evaporating in vacuo a solution mixture of the two isomers after that solution has been warmed for several hours.

EXAMPLE 3

5-(2,3-dihydroxyphenoxy)-1H-tetrazole and 5-(2,6-dihydroxyphenoxy)-1H-tetrazole A mixture of 22 g. of 5-(2,3-dimethoxyphenoxy)-1H-tetrazole or 5-(2,6-dimethoxyphenoxy)-1H-tetrazole, 40 g. of anhydrous aluminum chloride and 300 ml. of benzene was heated at 60° C. for two hours with vigorous stirring. The reaction mixture was decomposed by careful addition of 200 ml. of aqueous methanol (30% methanol), to free the product from a complex with aluminum chloride.

The product was extracted with ethyl acetate. The ethyl acetate was evaporated and the residue was dissolved in 15 ml. of hot water. Then the residue was treated with decolorizing carbon, filtered, and cooled. The product was obtained as colorless crystals with a melting point of about 195°–200° C. and weighed 9.5 g. (49% yield). NMR, carbon 13 NMR, elemental analysis, titration, and high pressure liquid chromatography identified the product as a mixture of 5-(2,3-dihydroxyphenoxy)-1H-tetrazole and 5-(2,6-dihydroxyphenoxy)-1H-tetrazole. Titration with base in 66% dimethyl-formamide gave the following results: $pK_a = 5.04$ and 11.87 and amw=200 (theory 194). The following elemental analysis was obtained:

Calculated for $C_7H_6O_3N_4$: Theory: N, 28.9, Found: N, 28.44.

EXAMPLE 4

5-(3,5-dihydroxyphenoxy)-1H-tetrazole

A mixture of 38.3 g. of 5-(3,5-dimethoxyphenoxy)-1H-tetrazole, 68 g. of anhydrous aluminum chloride, and 400 ml. of benzene was heated under reflux for about one and one-half hours. A mixture of 150 ml. of water and 30 ml. of methanol was added slowly to the aluminum chloride mixture. The solution was then stirred and allowed to cool. The aqueous layer was separated and extracted with ethyl acetate. After the ethyl acetate was evaporated, the product was crystallized from water. The weight of the product obtained was 28.2 g. and its melting point was 191°–193° C. The following elemental analysis was obtained:

Calculated for $C_7H_6O_3N_4 \cdot 2H_2O$: Theory: N, 24.3, Found: N, 24.25.

The salts of the 5-(dihydroxyphenoxy)-1H-tetrazole compounds are also effective sweeteners. Due to the acidity of these compounds, both inorganic and organic bases of sufficient basicity can be used to form the salts. The inorganic cations of choice are sodium, calcium, ammonium, and the like, while the organic bases can be selected from amines, alkaloids and the like. Therefore, the term "salts" includes inorganic and organic cations in combination with the tetrazole compound.

In particular, water-soluble salts are preferred, especially salts containing sodium, calcium, and ammonium, because water solubility is desirable in the typical use of a sweetener. The tetrazole salt is prepared by reacting the tetrazole compound with the selected base in an appropriate solvent.

The following examples illustrate the preparation of the salts.

EXAMPLE 5

5-(2,3dihydroxyphenoxy)-1H-tetrazole, sodium salt and 5-(2,6-dihydroxyphenoxy)-1H-tetrazole, sodium salt mixture A solution of 9.7 g. of a mixture of 5-(2,3-dihydroxyphenoxy)-1H-tetrazole and 5-(2,6-dihydroxyphenoxy)-1H-tetrazole and 4.2 g. of sodium bicarbonate in 100 ml. of water was concentrated in vacuo. The residual solid was identified as a mixture of sodium salts of the isomeric tetrazoles by elemental analysis and high pressure liquid chromatography. The solid weighed 10.8 g. and had a melting point of greater than 300° C. with decomposition. The following elemental analysis was obtained:

Calculated for $NaC_7H_5O_3N_4$: Theory: N, 25.9, Found: N, 25.5.

EXAMPLE 6

5-(2,3-dihydroxyphenoxy)-1H-tetrazole, sodium salt

A mixture of 9.7 g. of 5-(2,3-dihydroxyphenoxy)-1H-tetrazole and 5-(2,6-dihydroxyphenoxy-1H-tetrazole, 4.2 g. of sodium bicarbonate, and 100 ml. of ethanol was heated under reflux until carbon dioxide evolution ceased and a solution remained. Upon cooling, a crystalline material separated, was collected and dried. The material weighed 3.8 g. and melted with decomposition at a temperature greater than 250° C. It was identified as the sodium salt of 5-(2,3-dihydroxyphenoxy)-1H-tetrazole by high pressure liquid chromatography. Titration with base in 66% dimethylformamide gave the following: $pK_a=4.77$ and 11.71 and amw=219 (theory 216).

EXAMPLE 7

5-(2,3-dihydroxyphenoxy)-1H-tetrazole, calcium salt

A mixture of 9.7 g. of 5-(2,3-dihydroxyphenoxy)-1H-tetrazole and 5-(2,6-dihydroxyphenoxy)-1H-tetrazole, 2.5 g. of calcium carbonate, 100 ml. of ethanol and 25 ml. of water was heated under reflux until carbon dioxide evolution ceased and a solution was obtained. The solution was filtered and then cooled. There was obtained 5.5 g. of a crystalline product. It was identified by high pressure liquid chromatography (HPLC) as the calcium salt of 5-(2,3-dihydroxyphenoxy)-1H-tetrazole, with a melting point greater than 300° C.

The yield of the preferred compound, 5-(2,3-dihydroxyphenoxy)-1H-tetrazole, can be maximized from the mixture of 2,3- and 2,6-isomers by forming a salt. The sodium and calcium salts of the 2,3-isomer will selectively crystallize. Then if the salt is reacidified and worked-up quickly, almost 100% 5-(2,3-dihydroxyphenoxy)-1H-tetrazole is recovered. The following example illustrates the conversion from the salt to the 2,3-isomer.

EXAMPLE 8

5-(2,3-dihydroxyphenoxy)-1H-tetrazole

A mixture of 2.0 g. of 5-(2,3-dihydroxyphenoxy)-1H-tetrazole, calcium salt and 4.0 ml. of water was acidified with concentrated hydrochloric acid. The crystalline solid formed weighed 1.3 g. and had a melting point with decomposition of about 198°-200° C. Carbon 13 NMR and HPLC identified the solid as 5-(2,3-dihydroxyphenoxy)-1H-tetrazole.

One aspect of the present invention is directed to a method of sweetening an orally acceptable substance by adding to the substance an effective amount of a sweetening agent or sweetener of the formula

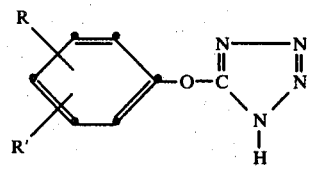

wherein R and R' are each hydroxy. Another aspect of the present invention is a method of administering essentially simultaneously to a warm-blooded animal an orally acceptable substance and an effective amount of a compound of the formula set forth above to provide a sweet taste. In yet another aspect, the present invention is directed to a composition comprising a preferred orally acceptable substance, a flavoring agent, and an effective amount of a sweetening agent of the above formula.

The identity of the orally acceptable substance in accordance with the present invention is not critical. In general, the term "orally acceptable substance" is employed herein to designate any substance which is taken partially or totally into the mouth cavity and which, in this context, is without any direct substantial toxicity. The substance can be one which is retained in or on the mouth for some period of time and is then removed such as, chewing gum, toothpaste, lip cosmetics, mouthwash, mouthspray, substances used in dentistry for cleansing of teeth, denture treating substances, chewing tobacco and other tobacco products, or the like. Pet toys, for example, rubber dog bones, as well as other mechanical devices temporarily retained within the mouth, are also orally acceptable substances in accordance with the present invention. Similarly, glues and adhesives, as for use on stamps and envelopes, are orally acceptable substances in accordance with the present invention. Alternatively, the orally acceptable substance can be one which is not only taken in the mouth cavity, but which, with or without mastication, is swallowed.

While the orally acceptable substance in accordance with the present invention can be any of a broad scope, as set forth above, including mechanical structures, a preferred orally acceptable substance is one which is a flavoring agent. The flavoring agent can be one which is contained in, as an inherent part of, a food; or the flavoring agent can be one specifically added to a substance, as, for example, a flavoring agent added to a chewing gum. This dual usage of the term "flavoring agent" as identifying either a food, or a substance added to a food, is in accordance with the terminology of this art (see Kirk-Othmer Encyclopedia of Chemical Technology, 2nd Edition, Interscience Publishers, Division of John Wiley & Sons, Inc., New York, 1966, Volume 9, page 347 and following).

There are, of course, numerous orally acceptable substances wherein the sole or main ingredient, other than inert substances such as water, thickening agents, and the like, is a flavoring agent. Attention is directed to coffee and tea. Thus, in accordance with the present invention, coffee, tea, fruit ades, or similar non-nutritive liquids of which the essential characteristic is a flavoring agent, can be sweetened with the present active agent. Furthermore, there are non-nutritive solid or semi-solid compositions such as salad dressings of which a main and essential constituent is a flavoring agent. Such compositions can be sweetened with the present active agent. The active agent can also be added to carbonated beverages of which a primary ingredient, or sole ingredient other than carbonated water, is a flavoring agent. In this sense, "flavoring agent" is used to describe a substance which has a discernible and desirable flavor at a concentration in liquids of 250 ppm or less, even though in other specialized applications, such as chewing gum, and highly flavored baked goods, higher concentrations may be used.

Representative flavoring agents include spices and herbs; the essential oils and their extracts; fruit-derived flavorings; plant extracts, as, for example, cola, caffeine, etc.; and synthetic flavorings, including those which simulate or duplicate the effective components of the flavoring agents of the previous categories. Attention is directed to Food Technology, 19, part 2, page 155 (1965), which lists substances generally recognized as safe for food additive purposes, including flavoring agents as well as other food additives which serve as bulking agents, etc.

The flavoring agent with which the present sweetening agent is combined can also be a nutritive component of a food. In this sense, then, the present invention is directed to formulations comprising the present sweetening agent, plus a food comprising as an inherent part thereof a flavoring agent.

Thus, for example, the food can be a nutritive solid. Such nutritive solid can be any of a great variety of foods, including baked goods such as bread, crackers, pretzels, pastries, or cake; cereal products; milk derived products, such as ice cream, ice milk, sherberts, custards and other puddings; gelatin products; and processed vegetables and fruits, such as, for example, canned tomatoes, frozen vegetables, and the like. Such nutritive solid foods include meat products in which a sweetening substance is incorporated during processing, such as ham and bacon. The nutritive solid in accordance with this invention also comprehends prepared "mixes" such as mixes for puddings, cakes, pastries, and the like; and confectionary products for example popcorn, peanut candies, chocolate candies, jellybeans, gumdrops, candy cigarettes, taffy, licorice, and the like. Furthermore, in accordance with the present invention, the term nutritive solid is inclusive of natural sugar and glycine and other amino acids which are nutritive. The nutritive solid can also be a feed, such as a grain-type feed silage, or other feed, for lower warm-blooded animals. The present active agent can also be added to specialized types of lower, warm-blooded animal feeds, such as salt licks, and can be used in baits as an attractant. In the instance of domestic animals such as dogs, the active agent can be added to regular feeds or to pet snack-type foods.

The food which comprises the flavoring agent can also be a nutritive liquid. Representative nutritive liquids include fruit and vegetable juices; alcoholic beverages such as beer, wine, cocktails and cocktail mixes, milk beverages such as milkshakes, "nogs," and the like; and where nutritive in character, carbonated beverages containing flavorings.

The present active agent can also be combined with a medicinal substance as an orally acceptable substance. Such medicinal substances can be a solid, such as a tablet, capsule, powder, or lozenge, including cough drops. The medicinal substance can also be a liquid; for example, an elixir, syrup, suspension, and the like. In this sense, "medicinal substance" is inclusive of veterinary substances for lower, warm-blooded animals.

The method of administration is not critical. The present non-nutritive agent is conveniently formulated as a tablet or capsule, and in this form, is especially suited for use with liquid substances. Thus, for example, the desired benefits of the present invention are obtained by adding a tablet of appropriate amount to a liquid, such as, for example, coffee. Such addition can be done on an individualized per-cup or per-glass basis. The present non-nutritive agent is equally well adapted to be formulated as a liquid formulation, typically an aqueous formulation, a suitable amount of which can be added to a solid or liquid food, and mixed therewith prior to consumption. In addition, the present non-nutritive sweetener is conveniently prepared as a free-flowing powder, which can then be shaken over and if desired mixed into an orally acceptable substance. It is, of course, also possible to incorporate the present active agent in pre-prepared mixes such as cake mixes, pudding mixes and the like, for home and/or industrial food preparation usage. Furthermore, the present non-nutritive sweetener can be employed in the processing of substances which are orally acceptable initially or after processing; as examples, ham and tobacco products are mentioned.

In order that the present active agent give the desired sweetening effect to the orally acceptable substance, it is necessary that the non-nutritive sweetener be taken into the mouth cavity at essentially the same time as the orally acceptable substance is taken into the mouth cavity. It is preferred that the substance and the sweetening agent be mixed before being taken into the mouth, but this is not critical.

The amount of the present non-nutritive sweetener to be employed is not critical either, it being necessary only that an effective amount is used. Generally, an effective amount is that amount which provides a sense of sweetness comparable to that afforded by sucrose at a given usage rate. Sucrose, of course, is used in a very wide range of concentrations in various orally acceptable substances. Thus, for example, in confectionary products sucrose concentration may approach 100 percent, whereas in many common foods and liquids, the sucrose concentration may be as low as 1 percent or lower, even so low as to be negligible. Correspondingly, the amount of the present active agent which will provide sweetness equivalent to that afforded by sucrose also varies widely. The amount of the present active agent to be used will also depend upon such variables as the particular animal ingesting the agent and the purpose of sweetening. The 5-(dihydroxyphenoxy)-1H-tetrazole compounds of the present invention are from about 100 to about 600 times as sweet as sucrose. The preferred compound, 5-(2,3-dihydroxyphenoxy)-1H-tetrazole is about 1,000 times sweeter than sucrose. Concentrations of sucrose were compared to various concentrations of the tetrazole compounds by a panel of one to determine the relative sweetness of the tetrazoles.

The compounds of the present invention can be employed as the sole sweetening agent or can be employed jointly with other sweeteners such as: saccharin-type; cyclamate-type; dihydrochalcone-type; monohydroxyphenoxy-1H-tetrazole compounds; 5-carbocyclicaminotetrazole compounds; and dextro enantiomorphs of 6-substituted tryptophane compounds.

When the active agent in accordance with the present invention is used in conjunction with another non-nutritive sweetener, the exact ratio of the components is not critical and can vary considerably, depending upon the animal, the type of orally acceptable substance, and the like. A synergistic effect is often noted when non-nutritive sweetening substances are combined. Thus, for example, when sodium saccharin is employed alone a concentration of 0.1 percent by weight is necessary to obtain a desirable sweet taste; and sodium cyclamate alone requires a concentration of 0.25 percent by weight. Yet combined, the same level of sweetness is obtained at a concentration of 0.01 percent of sodium saccharin and 0.1 percent of sodium cyclamate, both concentrations by weight (see U.S. Pat. No. 2,803,551).

It is known that the use of saccharin as a sweetening agent is accompanied by bitter aftertaste, experienced by a certain portion of the population. Since for many applications, the substance is ideally suited to usage as a sweetener, methods of diminishing the aftertaste have been studied. Attention is directed to British Pat. No. 1,091,154 and to U.S. Pat. No. 3,329,508 as examples. Therefore, in those unusual situations wherein the active agent in accordance with the present invention is accompanied by aftertaste, known methods of diminishing such aftertaste can be utilized. Furthermore, such methods can also be used where the present active agent is combined with saccharin and/or other non-nutritive sweeteners.

It is also possible to combine the present active agent with sucrose or other nutritive sweeteners so as to obtain a sweetening substance of reduced caloric value.

I claim:
1. A method which comprises orally administering
   a. an orally acceptable substance and
   b. 5-(2,3-dihydroxyphenoxy)-1H-tetrazole, or a mixture of 5-(2,3-dihydroxyphenoxy)-1H-tetrazole and 5-(2,6-dihydroxyphenoxy)-1H-tetrazole, or a non-toxic, physiologically acceptable salt thereof, said compound, mixture, or salt being administered in an amount sufficient to impart a desired degree of sweetness to the orally acceptable substance.
2. The method of claim 1 wherein the compound is 5-(2,3-dihydroxyphenoxy)-1H-tetrazole.
3. The method of claim 1 wherein the compound is a mixture of 5-(2,3-dihydroxyphenoxy)-1H-tetrazole and 5-(2,6-dihydroxyphenoxy)-1H-tetrazole.
4. A composition comprising
   a. a flavoring agent and
   b. 5-(2,3-dihydroxyphenoxy)-1H-tetrazole, or a mixture of 5-(2,3-dihydroxyphenoxy)-1H-tetrazole and 5-(2,6-dihydroxyphenoxy)-1H-tetrazole, or a non-toxic, physiologically acceptable salt thereof, said compound, mixture, or salt being present in an amount sufficient to impart a desired degree of sweetness to the composition.
5. The composition of claim 4 wherein the compound is 5-(2,3-dihydroxyphenoxy)-1H-tetrazole.
6. The composition of claim 4 wherein the compound is a mixture of 5-(2,3-dihydroxyphenoxy)-1H-tetrazole and 5-(2,6-dihydroxyphenoxy)-1H-tetrazole.
7. The composition of claim 4 wherein the flavoring agent is a nutritive solid.
8. The composition of claim 4 wherein the flavoring agent is a nutritive liquid.
9. The composition of claim 4 wherein the flavoring agent is essentially non-nutritive.
10. The composition of claim 4 wherein said composition is liquid.
11. The composition of claim 4 wherein said composition is solid.
12. A composition comprising
   a. as a first substance, 5-(2,3-dihydroxyphenoxy)-1H-tetrazole, or a mixture of 5-(2,3-dihydroxyphenoxy)-1H-tetrazole and 5-(2,6-dihydroxyphenoxy)-1H-tetrazole, or a non-toxic, physiologically acceptable salt thereof, and
   b. a second substance selected from the group consisting of:
      1. sucrose,
      2. a saccharin-type sweetener,
      3. a cyclamate-type sweetener,
      4. a dihydrochalocone-type sweetener,
      5. a monohydroxyphenoxy-1H-tetrazole,
      6. a 5-carbocyclicaminotetrazole, or
      7. a dextro enantiomorph of a 6-substituted tryptophane,
said substances being present in amounts sufficient, in combination, to impart a desired degree of sweetness to the composition.
13. The composition of claim 12 wherein the first substance is 5-(2,3-dihydroxyphenoxy)-1H-tetrazole.
14. The composition of claim 12 wherein the first substance is a mixture of 5-(2,3-dihydroxyphenoxy)-1H-tetrazole and 5-(2,6-dihydroxyphenoxy)-1H-tetrazole.
15. A composition comprising
   a. an orally acceptable substance, and
   b. 5-(2,3-dihydroxyphenoxy)-1H-tetrazole, or a mixture of 5-(2,3-dihydroxyphenoxy)-1H-tetrazole and 5-(2,6-dihydroxyphenoxy)-1H-tetrazole, or a non-toxic, physiologically acceptable salt thereof, said compound, mixture, or salt being in an amount sufficient to impart a desired degree of sweetness to the composition.

* * * * *